(12) United States Patent
Pietro

(10) Patent No.: US 8,747,906 B2
(45) Date of Patent: *Jun. 10, 2014

(54) DIETARY SUPPLEMENT ENHANCING THE MUSCULAR ENERGY METABOLISM, COMPRISING AN ALKANOYL CARNITINE AND RIBOSE

(71) Applicant: Sigma-Tau Industrie Farmaceutiche Riunite S.p.A., Rome (IT)

(72) Inventor: Pola Pietro, Rocca di Pappa (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,083

(22) Filed: Jul. 26, 2013

(65) Prior Publication Data

US 2013/0309216 A1 Nov. 21, 2013

Related U.S. Application Data

(60) Division of application No. 12/753,368, filed on Apr. 2, 2010, now Pat. No. 8,518,455, which is a division of application No. 11/604,390, filed on Nov. 27, 2006, now abandoned, which is a continuation of application No. 10/048,590, filed as application No. PCT/IT01/00283 on Jun. 1, 2001, now abandoned.

(30) Foreign Application Priority Data

Jun. 14, 2000 (IT) .................................. RM00A0323

(51) Int. Cl.
*A61K 38/00* (2006.01)

(52) U.S. Cl.
USPC ........................................................ 424/600

(58) Field of Classification Search
CPC ............................ A23L 1/236; A61K 31/7004
USPC .......................................................... 424/600
See application file for complete search history.

(56) References Cited

U.S. PATENT DOCUMENTS

| 6,159,942 A | 12/2000 | St. Cyr et al. |
| 6,245,378 B1 | 6/2001 | Cavazza |
| 6,541,029 B1 | 4/2003 | Namba et al. |
| 6,579,544 B1 | 6/2003 | Rosenberg et al. |

FOREIGN PATENT DOCUMENTS

| EP | 0 652 012 | 5/1995 |
| WO | 88/01861 | 3/1988 |
| WO | 94/15488 | 7/1994 |
| WO | 98/43499 | 10/1998 |
| WO | 99/65476 | 12/1999 |

OTHER PUBLICATIONS

St. Cyr et al., "Enhanced High Energy Phosphate Recovery with Ribose Infusion after Global Myocardial Ischemia in a Canine Model" J. Surg. Feb. 1989; 46(2): 157-62.

Ferrari et al., "The effect of propionyl-L-carnitine on the ischemic and reperfused intact myocardium and on their derived mitochondria" Cardiovasc. Drugs Ther. Feb. 1991; 5 Suppl 1:57-65.

*Primary Examiner* — Jake Vu

(74) *Attorney, Agent, or Firm* — Lucas & Mercanti, LLP

(57) ABSTRACT

A method for treating myocardial or skeletal muscle anoxia which occurs in coronary or post-infarct disorders or during prolonged physical activity and muscle fatigue. This method comprises the administration of a combination composition comprising (a) an alkanoyl L-carnitine selected from the group consisting of isovaleryl L-carnitine, propionyl L-carnitine or the pharmacologically acceptable salts thereof or mixtures thereof; and (b) ribose or a phosphate derivative thereof.

12 Claims, No Drawings

DIETARY SUPPLEMENT ENHANCING THE MUSCULAR ENERGY METABOLISM, COMPRISING AN ALKANOYL CARNITINE AND RIBOSE

CROSS-REFERENCE TO RELATED APPLICATIONS

This application is a divisional of a U.S. patent application Ser. No. 12/753,368 filed on Apr. 2, 2010, which is a divisional of U.S. application Ser. No. 11/604,390 filed on Nov. 27, 2006, which is a continuation-in-part of U.S. application Ser. No. 10/048,590 filed on Feb. 1, 2002, now abandoned, which is a 35 U.S.C. §371 national phase of PCT/IT01/00283 filed on Jun. 1, 2001, which claims priority to and the benefit of Italian Application No. RM2000A000323 filed on Jun. 14, 2000, the contents of each of which are incorporated herein by reference.

BACKGROUND OF THE INVENTION

The present invention relates to a health food/dietary supplement comprising as its characterising ingredients an alkanoyl L-carnitine selected from the group consisting of isovaleryl L-carnitine and propionyl L-carnitine or their pharmacologically acceptable salts or mixtures of the same and a monosaccharide pentose, particularly ribose or its phosphorylated analogues.

It has been found that the above-mentioned composition is extremely effective in exerting a potent stimulation of muscular energy metabolism, and can thus be profitably used in the prevention of myocardial insufficiency and in post-infarct conditions, as well as in the course of prolonged muscular effort during physical and sporting exercises, owing to the unexpected synergistic effect exerted by its components.

Isovaleryl L-carnitine, a natural component of the pool of carnitines, presents specific activity at lysosomal level and on the cytosolic movements of calcium. It is therefore capable of intervening in proteolytic processes such as occur during intense, prolonged effort and of protecting a number of organs, such as the liver, against the action of toxic substances. Propionyl L-carnitine exerts an intense antioxidant effect and is particularly effective in enhancing the peripheral circulation and cardiac functional capacity.

Moreover, muscular carnitine transferase possesses a greater affinity for propionyl L-carnitine than for L-carnitine, and consequently propionyl L-carnitine possesses a higher degree of specificity for cardiac and skeletal muscle. In addition, propionyl L-carnitine transferase, transporting the propionyl group, increases the uptake of this component by the muscle cells, which may be of particular importance for energy purposes, in that the propionate can be used by the mitochondria as an anapleurotic substrate and provide energy in the absence of oxygen.

Equally well known are the metabolic effects of ribose. Ribose is a monosaccharide pentose which is important in the body for the synthesis of nucleotides and other metabolic products. It is formed by conversion of glucose via the pentose phosphates. In the presence of a ribokinase ribose is phosphorylated to ribose-5-phosphate which, through the production of 5-phosphoribosyl-1-pyrophosphate (PRPP), can be used for the synthesis of nucleotides necessary for the production of ATP. PRPP, in addition to intervening in the production of ATP, is also important for the synthesis of nucleotides such as adenine and hypoxanthine and of ribonucleotides and deoxyribonucleotides.

It has now been found surprisingly that a composition comprising a combination of the following as its characterizing components:

(a) an alkanoyl L-carnitine selected from the group comprising isovaleryl L-carnitine, propionyl L-carnitine or their pharmacologically acceptable salts or mixtures of the same; and (b) ribose or one of its phosphorylated derivatives thereof, constitutes an effective health food/dietary supplement for the prevention of states of myocardial or skeletal muscle dysfunction related to conditions of anoxia or insufficient energy supply as occurring in coronary or post-infarct disorders or during prolonged physical activity and muscle fatigue, owing to the potent and unexpected synergistic effect exerted by its components.

The weight-to-weight ratios of the above-mentioned components (a):(b) range from 1:1 to 1:10.

The dietary supplement according to the present invention may additionally contain (c) a "carnitine" selected from the group comprising L-carnitine, acetyl L-carnitine, butyryl L-carnitine and valeryl L-carnitine, or their pharmacologically acceptable salts or mixtures of the same.

The weight-to-weight ratios of the above-mentioned components (a):(b):(c) range from 1:1:1 to 1:10:2.

The surprising synergistic effect achieved with the combination of "carnitines" (term denoting collectively both L-carnitine and the alkanoyl L-carnitines), particularly isovaleryl L-carnitine and/or propionyl L-carnitine, and ribose, has been demonstrated by several pharmacological tests (some of which are described here below) chosen in such a way as to prove strongly predictive for the purposes of the practical use of this composition in the preventive/nutritional/dietetic field.

In particular, this unexpected synergistic effect on the increase in energy capabilities at both cardiac and muscular level exerted by the combination according to the present invention enables it to be used in the prevention of both myocardial insufficiency and of muscle fatigue such as occur in cases of myocardial ischemia or in the course of intense muscular effort due to prolonged physical exercise or sporting activity.

DETAILED DESCRIPTION OF THE INVENTION

Test of ATP Concentrations in Heart Subjected to Anoxia

In this test the technique adopted was the one using papillary muscle of rabbit heart perfused and subjected to anoxia which, as is known, leads to an impoverishment of its ATP energy reserves. With this test, the aim was to observe whether or not preventive treatment with isovaleryl L-carnitine, with propionyl L-carnitine, with a carnitine combination or with ribose, or with a combination of these was capable of protecting cardiac muscle against the loss of ATP induced by anoxia.

In this test, a batch of New Zealand rabbits was used, subdivided into different groups which were injected intravenously every day for three consecutive days with isovaleryl L-carnitine alone (100 mg/kg), propionyl L-carnitine alone (100 mg/kg) or a carnitine combination consisting of propionyl L-carnitine (25 mg/kg), acetyl L-carnitine (25 mg/kg), L-carnitine (25 mg/kg), and isovaleryl L-carnitine (25 mg/kg) or with ribose alone (100 mg/kg), or ribose combined with the above-mentioned "carnitines".

At the end of the third day of treatment, all the animals were sacrificed and their hearts excised. Sections of papillary muscle measuring 1 mm in diameter and 4-5 mm in thickness were isolated from the excised hearts. The isolated papillary muscle was perfused in a thermostatic bath with a saturated 100% $O_2$ solution.

The anoxic state was obtained by introducing 100% $N_2$ instead of $O_2$ into the bath. For the measurement of the ATP concentrations in the papillary muscle the method described by Strehler was adopted (Strehler B. L. Methods in Enzymology 111 N.Y. Acad. Press., 879, 1957).

The analysis was carried out on tissue samples maintained in conditions of perfusion with oxygen for 90 minutes and after a period of anoxia of the same duration.

The results of this test, presented in Table 1, indicate that propionyl L-carnitine, isovaleryl L-carnitine, the carnitine combination and ribose are individually capable of partly protecting the ATP present in papillary muscle against anoxia, but that it was only with the combination of propionyl L-carnitine or isovaleryl L-carnitine plus ribose or with the combination of the carnitine combination plus ribose that complete protection against the anoxia-induced reduction in ATP could be obtained, thus demonstrating the potent synergistic effect exerted by the components of the combination.

TABLE 1

Test of ATP concentrations in papillary muscle of heart subjected to hypoxia

| Treatment | ATP concentration (mol/g tissue) | |
|---|---|---|
| | Before hypoxia | After hypoxia |
| Controls | 1.60 ± 0.55 | 0.41 ± 0.055 |
| Isovaleryl L-carnitine | 1.50 ± 0.60 | 0.55 ± 0.65 |
| Propionyl L-carnitine | 1.64 ± 0.79 | 0.60 ± 0.040 |
| Carnitine combination | 1.55 ± 0.50 | 0.62 ± 0.060 |
| Ribose | 1.62 ± 0.39 | 0.55 ± 0.075 |
| Isovaleryl L-carnitine + ribose | 1.50 ± 0.25 | 1.15 ± 0.055 |
| Propionyl L-carnitine + ribose | 1.61 ± 0.45 | 1.25 ± 0.35 |
| Carnitine combination + ribose | 1.65 ± 0.60 | 1.16 ± 0.30 |

Experimental Myocardial Anoxia Test

Adopting the technique described by Selych (Selych et al., Angiology, 11, 398, 1960) and modified by Clark (Clark C., J. Pharmacol. Methods, 3, 357, 1980), these tests were used to evaluate the protective activity of isovaleryl L-carnitine, propionyl L-carnitine, carnitine combination, ribose and various combinations of the same against ventricular arrhythmias induced by left coronary ligation in the rat.

Coronary occlusion and the resulting myocardial anoxia lead, after 5-8 minutes, to the onset of arrhythmias. In these tests, ventricular ectopic contractions were counted for a period of 30 minutes after ligation both in control rats and in rats that had received slow injections into the left ventricle, 15 minutes before ligation, of a solution containing isovaleryl L-carnitine alone (100 mg/kg), propionyl L-carnitine alone (100 mg/kg), or carnitine combination alone consisting of propionyl L-carnitine (25 mg/kg), acetyl L-carnitine (25 mg/kg) and isovaleryl L-carnitine (25 mg/kg) or ribose alone (100 mg/kg), or a combination of ribose plus isovaleryl L-carnitine or propionyl L-carnitine or a combination of ribose plus carnitine combination at the doses described above.

The results of this test (Table 2) indicate that, whereas isovaleryl L-carnitine alone or propionyl L-carnitine alone or carnitine combination alone or ribose alone produce only slight reductions in the number of ectopic contractions compared to controls, such contractions are reduced almost to the extent of disappearing altogether when ribose is injected in combination with isovaleryl L-carnitine, or propionyl L-carnitine, or carnitine combination, thus demonstrating the potent and unexpected synergistic effect exerted by the combination according to the present invention.

TABLE 2

Test of arrhythmia induced by myocardial anoxia

| Treatment | Start of arrhythmias after (mins) | N. of ectopic contractions during 30 minutes after ligation |
|---|---|---|
| Controls | 5-7 | 989 ± 96 |
| Isovaleryl L-carnitine | 5-7 | 860 ± 75 |
| Propionyl L-carnitine | 5-8 | 830 ± 86 |
| Carnitine combination | 5-8 | 810 ± 99 |
| Ribose | 5-7 | 855 ± 110 |
| Isovaleryl L-carnitine + ribose | 6-7 | 270 ± 95 |
| Propionyl L-carnitine + ribose | 6-8 | 230 ± 112 |
| Carnitine combination + ribose | 6-8 | 207 ± 93 |

Some non-limiting examples of compositions according to the present invention are given herein below:

Lozenges, capsules, tablets

| | | |
|---|---|---|
| 1) | Propionyl L-carnitine | 500 mg |
| | Ribose | 500 mg |
| 2) | Isovaleryl L-carnitine | 500 mg |
| | Ribose | 500 mg |
| 3) | Propionyl L-carnitine | 125 mg |
| | Acetyl L-carnitine | 125 mg |
| | L-carnitine | 125 mg |
| | Isovaleryl L-carnitine | 125 mg |
| | Ribose | 500 mg |

Granulates or vials

| | | |
|---|---|---|
| 4) | Propionyl L-carnitine | 1 g |
| | Ribose | 1 g |
| 5) | Isovaleryl L-carnitine | 1 g |
| | Ribose | 1 g |
| 6) | Propionyl L-carnitine | 1 g |
| | Ribose | 2.5 g |
| 7) | Propionyl L-carnitine | 250 mg |
| | Acetyl L-carnitine | 250 mg |
| | Isovaleryl L-carnitine | 250 mg |
| | L-carnitine | 250 mg |
| | Ribose | 2.5 g |
| 8) | Propionyl L-carnitine | 250 mg |
| | Acetyl L-carnitine | 250 mg |
| | Isovaleryl L-carnitine | 250 mg |
| | L-carnitine | 250 mg |
| | Ribose | 2 g |
| | Ribonucleic acid | 100 mg |
| | Deoxyribonucleic acid | 100 mg |
| 9) | Propionyl L-carnitine | 250 mg |
| | Acetyl L-carnitine | 250 mg |
| | Isovaleryl L-carnitine | 250 mg |
| | L-carnitine | 250 mg |
| | Ribose | 2 g |
| | L-glutamine | 100 mg |
| | L-alanine | 100 mg |
| | L-arginine | 100 mg |
| | L-glicine | 100 mg |
| | L-histidine | 100 mg |
| | L-isoleucine | 100 mg |
| | L-phenylalanine | 50 mg |
| | L-threonine | 50 mg |
| | L-serine | 100 mg |
| 10) | Propionyl L-carnitine | 250 mg |
| | Acetyl L-carnitine | 250 mg |
| | Isovaleryl L-carnitine | 250 mg |
| | L-carnitine | 250 mg |
| | Ribose | 1 g |

-continued

|  |  |  |  |
|---|---|---|---|
|  | Destrose | 0.5 | g |
|  | Fructose | 0.5 | g |
|  | Maltose | 0.5 | g |
| 11) | Propionyl L-carnitine | 250 | mg |
|  | Acetyl L-carnitine | 250 | mg |
|  | Isovaleryl L-carnitine | 250 | mg |
|  | L-carnitine | 250 | mg |
|  | Ribose | 1 | g |
|  | Glucose-1,6-diphosphate | 200 | mg |
|  | Fructose-1,6-diphosphate | 200 | mg |
|  | Galactose-1,6-phosphate | 200 | mg |
|  | Glycerol-3-phosphate | 200 | mg |
|  | Phosphenylpyruvate | 100 | mg |
|  | Thiamine pyrophosphate | 5 | mg |
|  | Pyridoxal-5-phosphate | 5 | mg |
|  | Magnesium stearate | 2 | mg |
| 12) | Propionyl L-carnitine | 250 | mg |
|  | Acetil L-carnitine | 250 | mg |
|  | Isovaleryl L-carnitine | 250 | mg |
|  | L-carnitine | 250 | mg |
|  | Ribose | 1 | g |
|  | Vit. A | 1250 | U.I. |
|  | Vit. $B_1$ | 0.5 | mg |
|  | Vit. $B_6$ | 30 | mg |
|  | Vit. C | 50 | mg |
|  | Vit. E | 5 | mg |
|  | Nicotinammide | 25 | mg |
|  | Vit. $B_{12}$ | 100 | mcg |
|  | Vit. D | 100 | U.I. |
|  | Pantothenic acid | 30 | mg |
|  | Magnesium glycinate | 5 | mg |
|  | Manganese | 1 | mg |
|  | L-Selenomethionine | 50 | mcg |
|  | Molybdenum | 10 | mcg |
|  | Zinc | 1 | mg |

What is meant by a pharmacologically acceptable salt of the various carnitines mentioned in the present invention, is, in addition to the respective inner salts, any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

Among these salts, isovaleryl L-carnitine acid fumarate (U.S. Pat. No. 5,227,518) is particularly preferred.

A list of FDA-approved pharmacologically acceptable acids is given in *Int. J. Pharm.*, 33, 1986, 201-217, the latter publication being incorporated in the present specification by reference.

The supplement of the invention may further comprise vitamins, coenzymes, mineral substances, aminoacids and antioxidants. The supplement may be manufactured in the form of tablets, lozenges, capsules, pills, granulates, syrups, vials or drops.

While the invention has been described in connection with what is presently considered to be the most practical and preferred embodiment, it is to be understood that the invention is not to be limited to the disclosed embodiment, but on the contrary, is intended to cover various modifications and equivalents arrangements included within the spirit and scope of the appended claims.

The invention claimed is:

1. A food/dietary supplement for the reduction of arrhythmia induced by myocardial anoxia, which comprises:
   (a) an alkanoyl L-carnitine selected from the group consisting of isovaleryl L-carnitine, and propionyl L-carnitine or the pharmacologically acceptable salts thereof or mixtures thereof; and
   (b) ribose,
   wherein the weight ratio of ingredients (a):(b) ranges from 1:1 to 1:10.

2. The supplement according to of claim 1, further comprising: (c) a carnitine selected from the group consisting of L-carnitine, acetyl L-carnitine, butyryl L-carnitine and valeryl L-carnitine or the pharmacologically acceptable salts or mixtures thereof.

3. The supplement according to of claim 2, wherein the weight ratio of ingredients (a):(b):(c) ranges from 1:1:1 to 1:10:2.

4. The supplement according to of claim 1, which further comprises vitamins, sugars, coenzymes, mineral substances, ammo acids, peptides and antioxidants.

5. The supplement according to of claim 1, wherein the pharmacologically acceptable salt is selected from the group consisting of: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mutate; orotate; oxalate; acid oxalate; sulphate, acid sulphate; trichloroacetate; trifluoroacetate and methane sulphonate.

6. A method for reducing arrhythmia induced by myocardial anoxia, comprising administering to an individual in need thereof the supplement according to claim 1.

7. A method for reducing arrhythmia induced by myocardial anoxia, comprising administering to an individual in need thereof a combination composition consisting of:
   (a) an alkanoyl L-carnitine selected from the group consisting of isovaleryl L-carnitine, and propionyl L-carnitine or the pharmacologically acceptable salts thereof or mixtures thereof; and
   (b) ribose,
   wherein the weight ratio of ingredients (a):(b) ranges from 1:1 to 1:10.

8. The method of claim 7, further comprising: (c) a carnitine selected from the group consisting L-carnitine, acetyl L-carnitine, butyryl L-carnitine and valeryl L-carnitine or the pharmacologically acceptable salts or mixtures thereof.

9. The method of claim 8, wherein the weight ratio of ingredients (a):(b):(c) ranges from 1:1:1 to 1:10:2.

10. The method of claim 7, wherein said combination compostion comprises vitamins, sugars, coenzymes, mineral substances, amino adds, peptides and antioxidants.

11. The method of claim 7, wherein the pharmacologically acceptable salt is selected from the group consisting of: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate; acid oxalate; sulphate, acid sulphate; trichloroacetate; trifluoroacetate and methane sulphonate.

12. The method of claim 7, wherein the combination compostion is in the form of tablets, capsules, lozenges, pills, granules, creams, syrups or drops.

* * * * *